US007972629B2

(12) United States Patent
Folan et al.

(10) Patent No.: US 7,972,629 B2
(45) Date of Patent: Jul. 5, 2011

(54) PRODUCT COMPRISING A COMBINATION OF MILK SERUM APOPROTEINS AND FREE FATTY ACIDS

(75) Inventors: Michael A. Folan, Donegal Town (IE); Damien Brady, Carlow Town (IE)

(73) Assignee: Westgate Biological Ltd. (IE)

( * ) Notice: Subject to any disclaimer, the term of this patent is extended or adjusted under 35 U.S.C. 154(b) by 0 days.

(21) Appl. No.: 12/657,884

(22) Filed: Jan. 30, 2010

(65) Prior Publication Data
US 2010/0209526 A1    Aug. 19, 2010

Related U.S. Application Data

(62) Division of application No. 10/487,616, filed as application No. PCT/IE02/00121 on Aug. 20, 2002, now Pat. No. 7,687,074.

(30) Foreign Application Priority Data

Aug. 23, 2001 (IE) .................................. S2001/0780

(51) Int. Cl.
*A61K 35/20* (2006.01)
*A61K 39/20* (2006.01)
*A61K 45/00* (2006.01)
*A61K 39/38* (2006.01)

(52) U.S. Cl. .............. 424/535; 424/157.1; 424/278.1; 424/184.1

(58) Field of Classification Search ........................ None
See application file for complete search history.

(56) References Cited

U.S. PATENT DOCUMENTS

| | | | |
|---|---|---|---|
| 2,796,378 A | 6/1957 | Ferguson, Jr. | |
| 4,397,927 A | 8/1983 | Brog | |
| 4,918,008 A | 4/1990 | Gauri | |
| 5,160,759 A * | 11/1992 | Nomura et al. | 426/602 |
| 5,667,797 A | 9/1997 | Peterson et al. | |
| 5,785,984 A | 7/1998 | Kurihara et al. | |
| 6,287,590 B1 | 9/2001 | Dasseux | |
| 6,319,895 B1 | 11/2001 | Tomita et al. | |
| 6,468,556 B1 | 10/2002 | Noda et al. | |
| 6,764,707 B1 | 7/2004 | Masui et al. | |
| 2001/0007690 A1 | 7/2001 | Girsh | |
| 2003/0031758 A1 | 2/2003 | Koss et al. | |
| 2003/0165606 A1 | 9/2003 | Lasekan et al. | |

FOREIGN PATENT DOCUMENTS

| | | |
|---|---|---|
| EP | 0572139 A2 | 12/1993 |
| EP | 1319407 A1 | 6/2003 |
| GB | 1050756 | 12/1966 |
| JP | 62-249931 A | 10/1987 |
| JP | 03-220130 A3 | 9/1991 |
| JP | 04-159232 A | 6/1992 |
| JP | 10-059865 A | 3/1998 |
| WO | 8604217 | 7/1986 |
| WO | 9604929 | 2/1996 |
| WO | 9904804 | 2/1999 |
| WO | 9926971 | 6/1999 |
| WO | 0000214 | 1/2000 |
| WO | 0048558 | 8/2000 |

OTHER PUBLICATIONS

Clerici et al. (Exp. Opin. Invest. Drugs, 1999; 8(2): 95-106).*
DeMets (*Chlamydia trachomatis*, Bacteriology at UW-Madison 330 Lecture Topic, http://www.bact.wisc.edu/bact330/lecturechlamydia, pp. 1-7; Aug. 2005).*
Deepe (Clinical Microbiology Reviews, 1997; 10(4): 585-96).*
Sprong C et al.: "Bacterial Activities of Milk Lipids", Antimicrobial Agents of Chemotherapy, vol. 45, No. 4, Apr. 2001, pp. 1298-1301, XP002235259 cited in the application Abstract.
Kanno et al., "Selective solubilisation of glycoproteins of milk fat globule membrane with KCI and MgCI2", Agric. Biol. Chem., 1980; 44(5); 1193-94.
Maruyama et al., "The effect of milk and skim milk intake on serum lipids and apoproteins in postmenopausal females", J. Nutr. Sci. Vitaminol., 1992; 38: 203-213.
Biervliet et al., "Serum cholesterol, cholesteryl ester and high-density lipoprotein development in newborn infants: response to formulas supplemented with cholesterol and gamma-linolenic acid", J. Pediatr., 1992: 120: S101-8.
Satoh et al., "Repression of fat-dependent intestinal Apo A-IV mRNA abundance by medium chain triacylglycerols and proteins and elevation by carbohydrates of fat-dependent Apo A-IV transport in suckling rat pups", J. Nutr. Sci. Vitaminol, 1995; 41: 293-306.
Wikipedia (http://en.wikipedia.org/wiki/whey_protein)—definition of whey protein.
http://www.healthscout.com/ency/68/312/main.html#PreventionofCandidaAlbicans; accessed Sep. 12, 2007.
Ellis, R, New Technologies for Making Vaccines, text book, 1998, pp. 568-575.
Boslego, J. et al., Gonorrhea Vaccines, 1988, Chapter 17, pp. 211-223.
Freshney, Culture of Animal Cells, A Manual of Basic Technique, Alar R. Liss, Inc., 1983, New York, p. 4.
Dermer, Bio/Technology, 1994, vol. 12, p. 320.
Fujimoto et al., J. Clin. Invest, 1993; 91: 1830-1833.
Nonnecke, B.J. et al., "Inhibition of mastic bacteria by bovine milk-apo-lactoferrin evaluated by in vitro microassay of bacterial growth", J. Dairy Sci., 1984, vol. 67, No. 3, p. 606-613.

* cited by examiner

*Primary Examiner* — Vanessa L. Ford
*Assistant Examiner* — Lakia Tongue
(74) *Attorney, Agent, or Firm* — Technology Law, PLLC.; Karen L. Kimble

(57) ABSTRACT

The present invention relates to use of a milk apoprotein or a mixture thereof to prevent or treat microbial or viral infection of the human or animal body. It is believed that this is achieved by inhibiting adhesion of potential pathogens. More preferably, at least one milk apoprotein or a mixture thereof is administered, simultaneously or sequentially, with either or both of at least one free fatty acid or a mixture thereof or a monoglyceride thereof; and/or at least one organic acid or a salt or ester thereof or a mixture thereof. The active agent(s) may be delivered by means of a pharmaceutically acceptable delivery system which includes parenteral solutions, ointments, eye drops, nasal sprays, intravaginal devices, surgical dressings, medical foods or drinks, oral healthcare formulations and medicaments for mucosal applications.

13 Claims, 7 Drawing Sheets

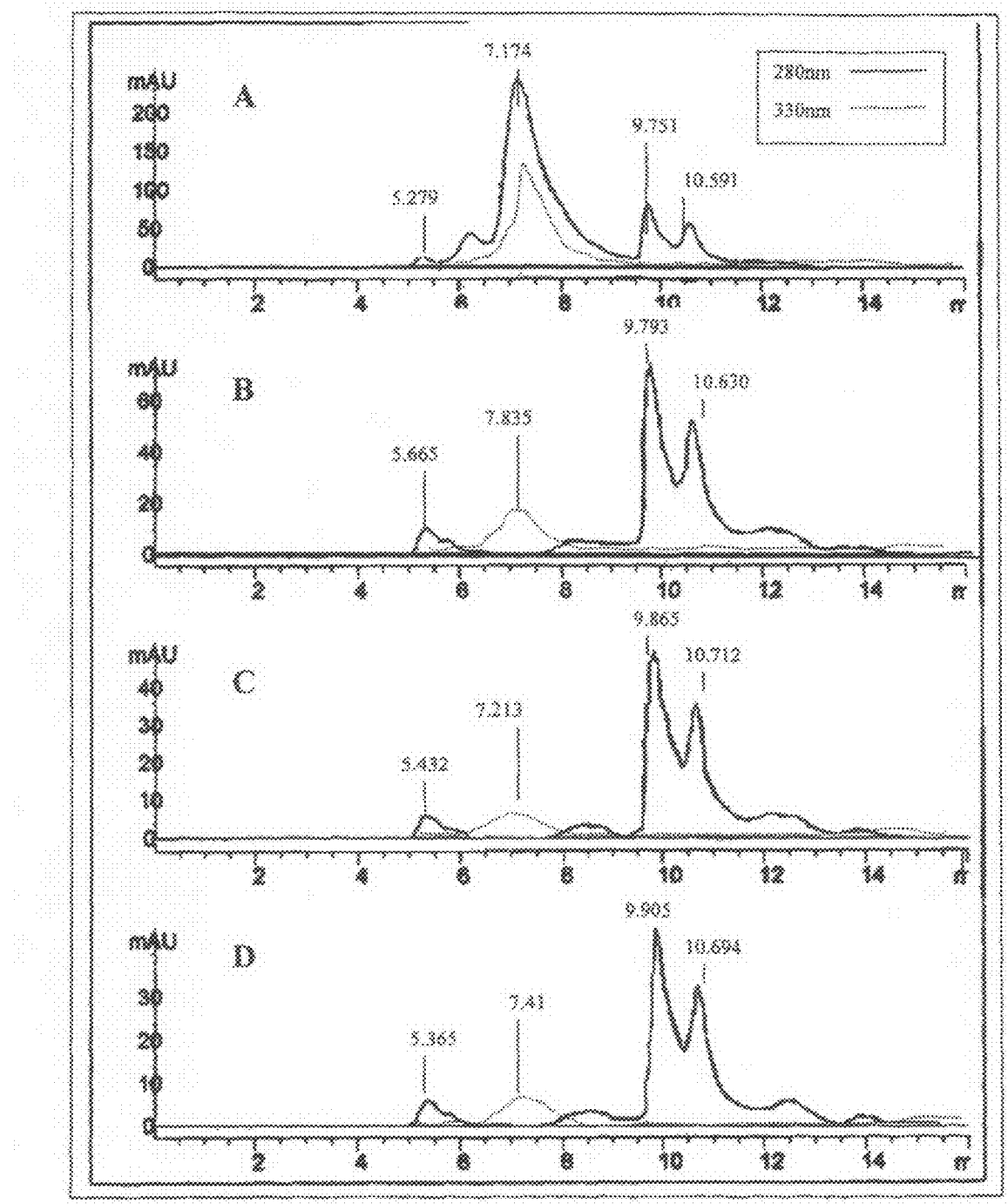

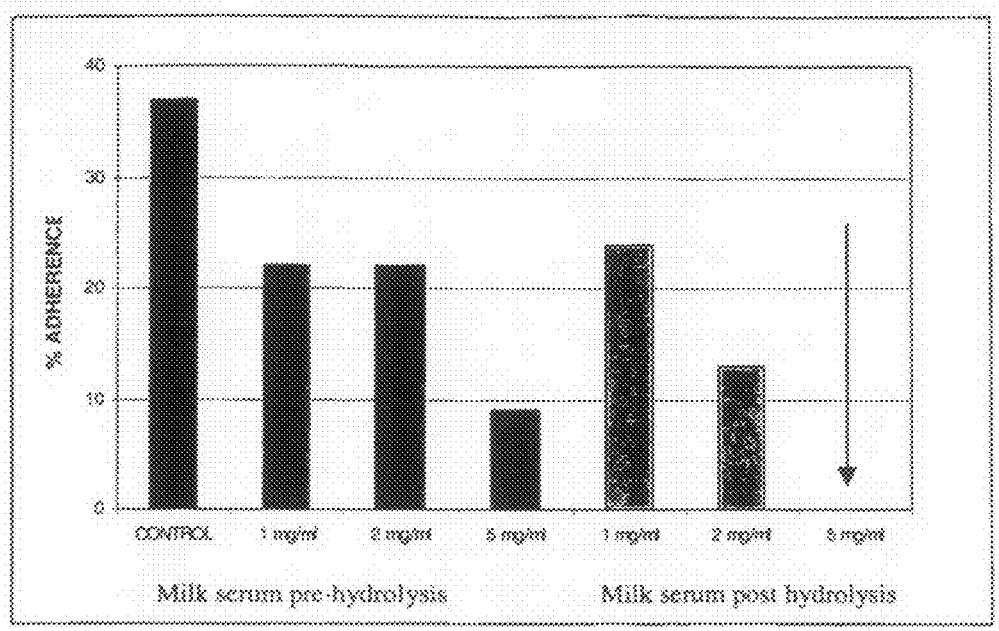
Diagram 2:
Inhibition of Adhesion: *Candida albicans*, pre and post enzyme hydrolysis of milk serum.
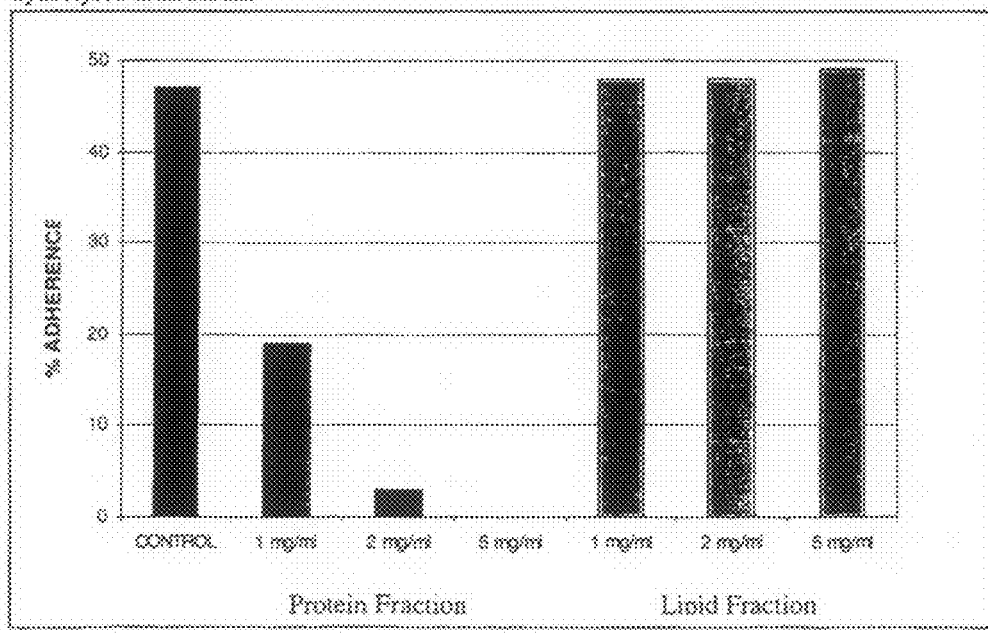
Diagram 3:
Inhibition of Adhesion: *Candida albicans*, protein Vs Lipid fraction from enzyme hydrolysed milk serum

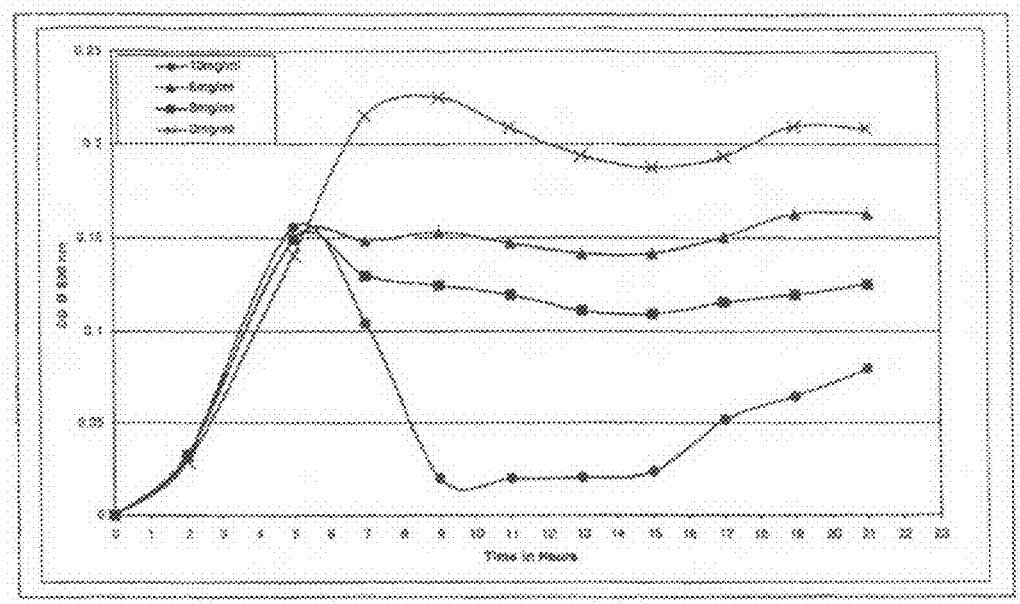
Diagram 4
Growth Inhibition: *Candida albicans*, Lipid Fraction of enzyme hydrolysed milk serum
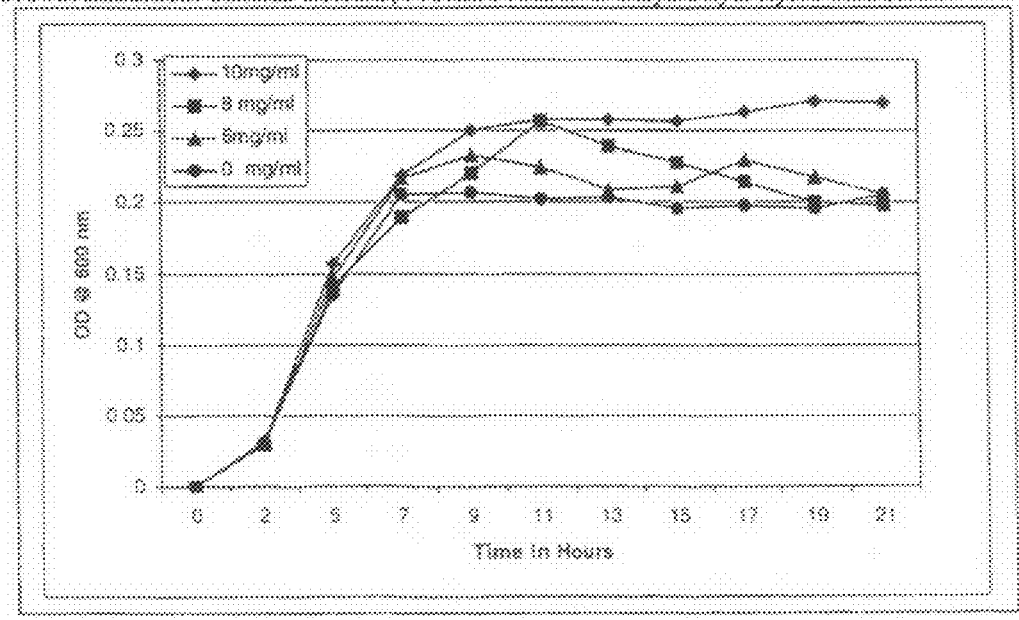
Diagram 5:
Growth Inhibition: *Candida albicans*, Protein Fraction of enzyme hydrolysed milk serum

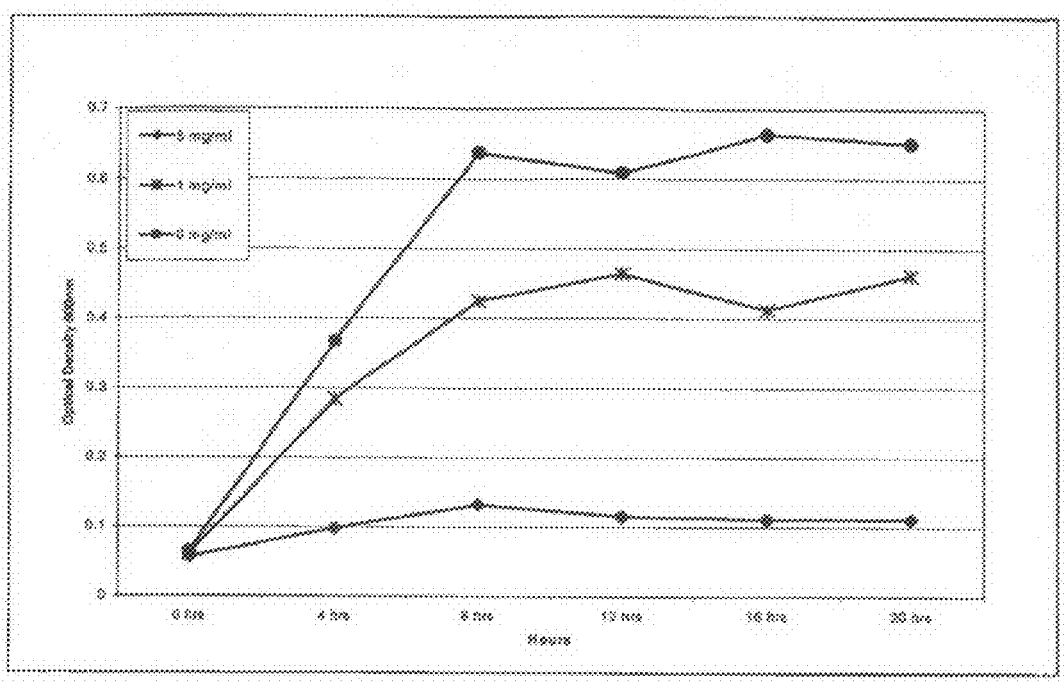
Diagram 6: Inhibition of Growth, *Candida albicans*: Standard Formulation.
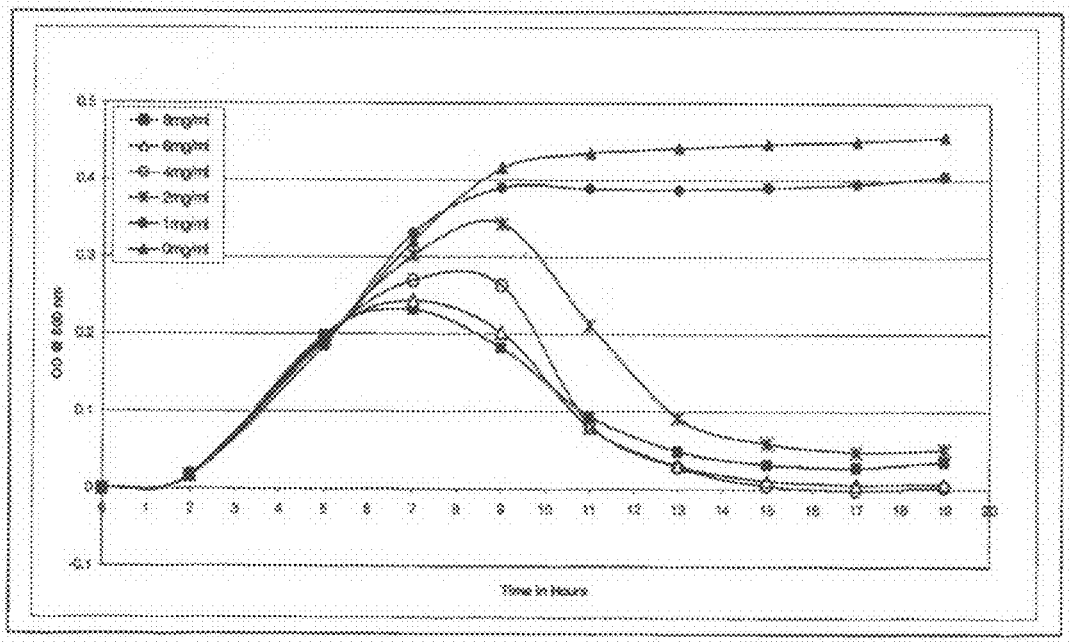
Diagram 7: Inhibition of Growth, *Candida albicans*: Intervention assay at 5 hours.

Diagram 8:
Inhibition of Adhesion: Pre-treatment of *Candida albicans*: Standard Formulation
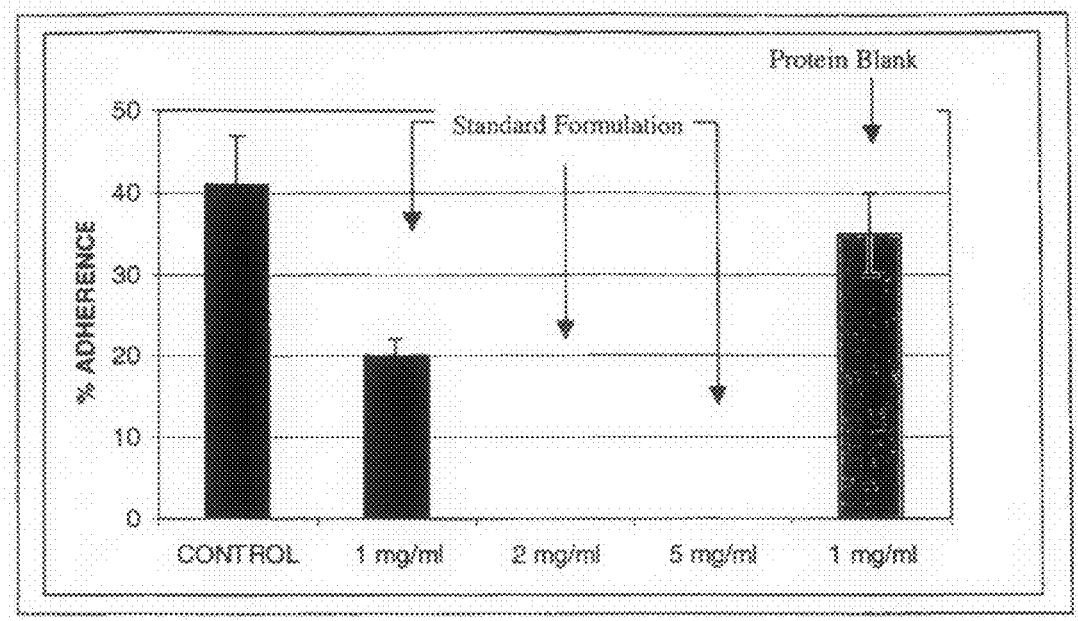
Diagram 9:
Inhibition of Adhesion: Pre-treatment of Buccal Epithelial Cell: Standard Formulation
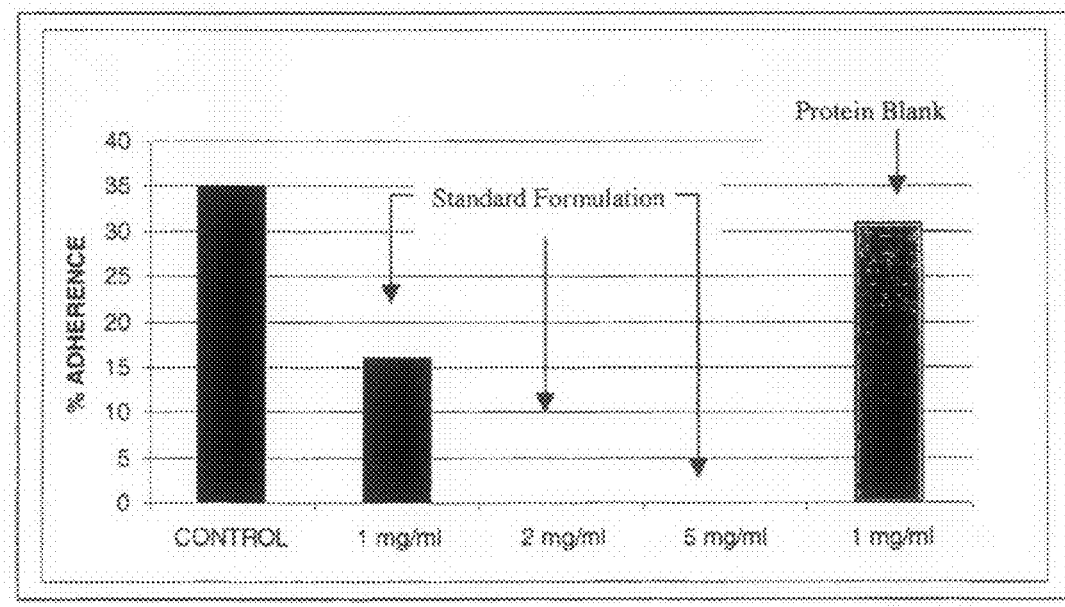

Diagram 10:
Inhibition of Growth: Methicillin Resistant *Staphylococcus aureus*:
Standard Formulation supplemented with Sodium Citrate.
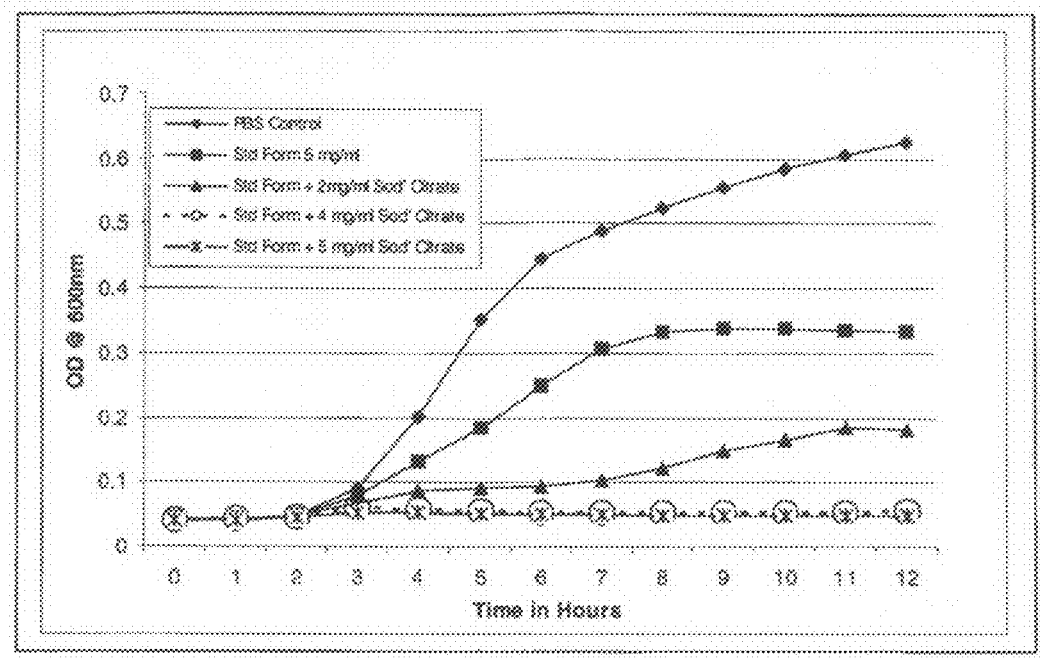
Diagram 11:
Inhibition of Adhesion: Methicillin resistant *Staphylococcus aureus* to buccal Epithelial Cell
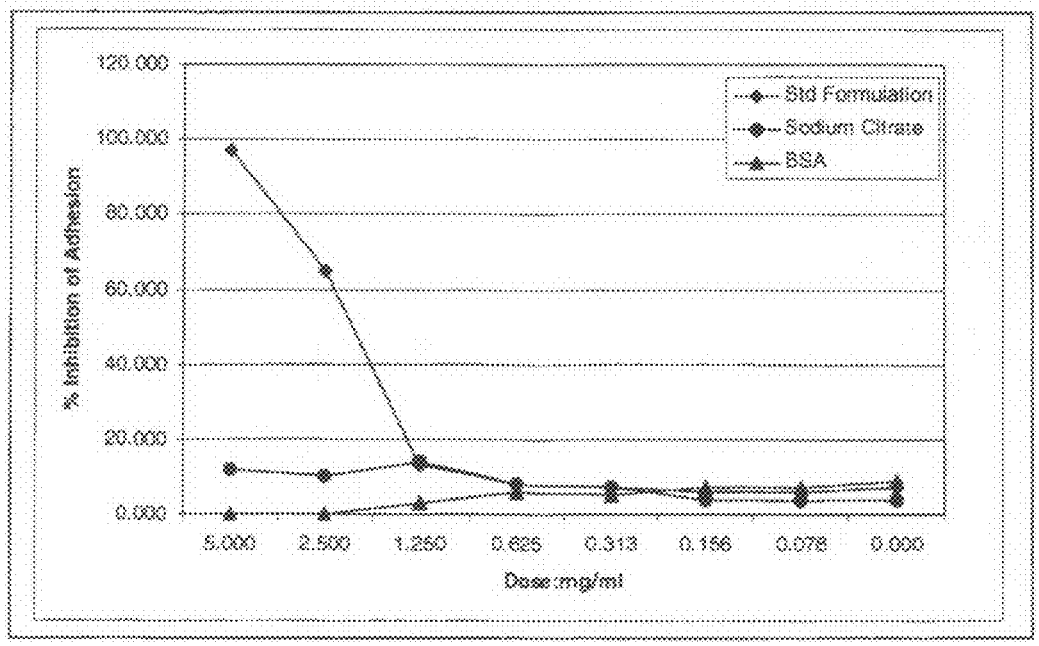

Diagram 12: Inhibition of growth: *Streptococcus mutans*: Standard Formulation
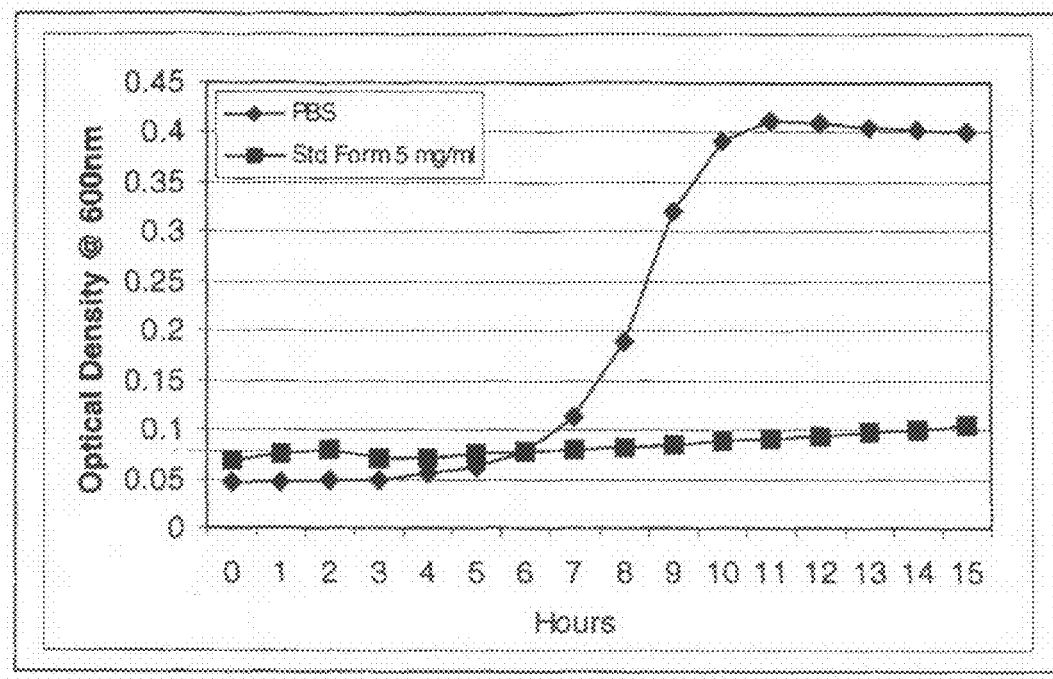
Diagram 13:
Inhibition of Adhesion, *Streptococcus mutans* to Hydroxyapatite beads: Standard Formulation
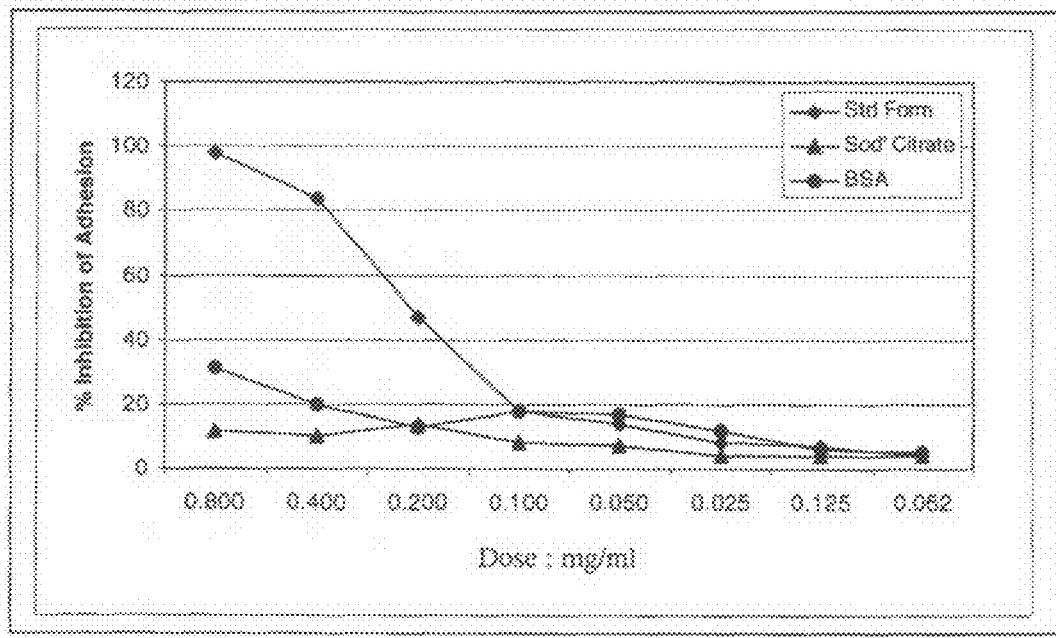

PRODUCT COMPRISING A COMBINATION OF MILK SERUM APOPROTEINS AND FREE FATTY ACIDS

CROSS REFERENCE TO RELATED APPLICATIONS

This application claims priority from all the following listed applications and is a divisional application of U.S. Ser. No. 10/487,616, filed Oct. 18, 2004 now U.S. Pat. No. 7,687,074, which is a national phase application from International Application PCT/IE2002/00121, filed 20 Aug. 2002 (now expired), which claims priority from Irish Application S2001/0780, filed 23 Aug. 2001.

This invention relates to the use of milk apoproteins to prevent or treat microbial or viral infection of the human or animal body. More specifically, these milk apoproteins may be used alone or in combination with one or more short chain organic acids and their salts or esters such as citric acid and/or one or more free fatty acids and their monoesters for inhibiting adhesion and/or growth of potential pathogens.

BACKGROUND ART

Milk is a whitish liquid that is produced from the mammary glands of mature female mammals after they have given birth. Mammals are warm-blooded vertebrates of the Class Mammalia, including humans, the mammals, for the purposes of the present invention, being more preferably hoofed, even-toed mammals of the Suborder Ruminantia, such as cattle, sheep, goats, deer and giraffes Milk from cattle and goats are the preferred sources of milk apoproteins of the present commercial scale.

Milk serum is a term commonly used in the dairy industry to describe the clear liquid matrix within which casein micelles and butterfat globules are suspended. Milk serum from ruminants contains the milk sugar lactose; a variety of proteins including milk antibodies, lactoferrin and enzymes; and a variety of lipoproteins including beta-lactoglobulin. Milk serum is a preferred source of milk apoproteins.

Cow's milk is processed in the dairy industry to obtain either butter or cheese. Mechanical agitation is used to break the milk-fat globules to obtain butter, and casein is precipitated to obtain curd from which cheese is manufactured. The liquid residue remaining after these processes is commonly referred to as milk whey. Milk whey is essentially the milk serum, with an increased lipoprotein content arising mainly from the fat globule membrane. Milk whey is a preferred source of milk apoproteins. The term "milk serum apoprotein" as used herein is intended to embrace milk apoproteins derived from milk serum or milk whey.

There are a variety of different lipoproteins and glycoproteins in milk serum, all of which are characterised by a protein back-bone, to which lipids and/or carbohydrates are conjugated. Enzymatic hydrolysis may be used to remove the lipids and/or carbohydrates from this protein back-bone, to prepare the corresponding apoprotein. Although milk serum apoproteins have been isolated, there are no known medical uses for such milk serum apoproteins.

Lipids, or fats, include triesters of fatty acids, which may be the same or different, and glycerol, also described as tri-acylglycerols or triglycerides. Further hydrolysis may be used to break these ester bonds, thus liberating free fatty acid(s) from the tri-acylglycerols. The use of calf pregastric lipase to liberate free fatty acids from milk lipids is reported by Cynthia Q Sun et al (Chemico-Biological Interactions 140 (2002), pp 185-198). This author reports the growth inhibitory properties of various free fatty acids against Enterococci, which are gram-positive, and coliform bacteria, which are gram-negative but is silent on the role of milk serum apoproteins.

Free fatty acids are known to exhibit potent antimicrobial and antiviral activity. In particular, linoleic, linolenic, caprylic and caproic acids were reported by Schuster et al (Pharmacology and Therapeutics in Dentistry 5: pp 25-33; 1980) to inhibit the dental caries organism, *Streptococcus mutans*, and to effect a general reduction in dental plaque. According to the author, bacteria classified as gram negative are most sensitive while gram positives are least affected. Additionally, Halldor Thormar et al (Antimicrobial Agents and Chemotherapy; January 1987, pp 27-31) review the antiviral properties of free fatty acids and their monoesters, demonstrating the efficacy of polyunsaturated long-chain fatty acids and medium-chain saturated fatty acids (and their monoglyceride esters) against enveloped viruses and their relative inactivity against nonenveloped viruses, the viricidal effect being possibly by destabilising the viral envelope itself More recently, the bactericidal activity of free fatty acids was reviewed by R. Corinne Sprong et al (Antimicrobial Agents and Chemotherapy, April 2001, pp 1298-1301)-C10:0 and C12:0 fatty acids were found to be powerful bactericidal agents. The fungicidal properties of C10:0 and C12:0 free fatty acids and their monoglycerides was described by Gudmundur Bergsson et al (Antimicrobial Agents and Chemotherapy, November 2001, pp 3209-3212).

Many potentially pathogenic bacteria are common commensals of the skin, hair and mucus membranes—they colonise these areas by adhering to the surface epithelial cell layer but are normally kept in check by the host's secretory immune system in mucus and sweat. Disease caused by these endogenous species usually arises as a result of some debilitation in the host's secretory immune capability, which allows these endogenous pathogens to proliferate.

Adhesion of pathogenic bacteria to host tissue is generally accepted as being the first stage in pathogenesis, so that the ability to block adhesion should be useful in preventing infection. The mechanism of such adhesion is varied and many organisms employ a multiplicity of both specific and non-specific factors. For example, Staphylococci secrete an extracellular teichoic acid, which binds specifically to fibronectin; *Candida* species employ a glycocalyx of mannoprotein; and Streptococci make use of water insoluble glucans to colonise the teeth. Because of the variety of these factors, it has long been considered impossible to devise a single inhibitor, which would be effective against the wide range of potentially pathogenic species.

The use of antibodies derived by vaccination of some donor animal has been attempted in many situations but, because of the built in specificity, the therapeutic use of these antibodies is confined to use against the species to which they have been generated.

In all of the above published data, the use of free fatty acids to inhibit growth of a wide range of bacteria, fungi and viruses is disclosed but there are no known published data disclosing or suggesting their efficacy when administered with one or more milk apoproteins in the inhibition of adhesion and/or growth of potential pathogens in human and animal healthcare.

The common practice in medical and veterinary care of infection is the application of an antibiotic substance designed to inhibit the infectious agent, which may be fungal, bacterial (both embraced by the term "microbial") or viral. In long-term use, many antibiotic substances have lost their potency due to the evolution of resistance by the infectious agent. The problem of antibiotic resistance is most acute in post-operative situations where the infectious agent is a common inhabitant of the skin and respiratory tract and, as such, it may have been exposed to frequent and varied antibiotics over time, allowing it to evolve resistance to these substances. Large numbers of these normally innocuous agents may be disseminated during surgical or nursing procedures and may give rise to infections when the immune tolerance of the patient has been weakened by disease or extended medical intervention; such infections are frequently described as nosocomial infections.

One such nosocomial infection is commonly referred to as MRSA (methicillin resistant *Staphylococcus aureus*). *Staphylococcus aureus* is a common inhabitant of the respiratory tract of many individuals, where it is carried asymptomatically without normally causing infection. Because of its ubiquitous nature, it is thought to have been exposed to many of the commonly used antibiotic substances, and strains now exist which are resistant to all commonly used antibiotics including methicillin Vancomycin is 'the drug of last resort' in MRSA, but strains have recently emerged that are resistant to vancomycin. In addition, vancomycin resistant *Enterococcus faecalis* (VREF) is a common inhabitant of the gut and may be disseminated from there during surgical procedures, giving rise to other nosocomial infection.

Horizontal gene transfer is a biological term used to describe the potential transfer of genetic resistance from one species to another. The transfer of antibiotic resistance from species such as VREF to pathogenic species such as *Clostridium difficile* (*Pseudomembranous colitis*) is a potentially disastrous event and one which gives cause for great concern among the medical profession.

There is therefore a great need for new antimicrobial substances, which may be used to treat such antibiotic resistant infections and others that are refractive to conventional treatments, and for new antiviral substances to treat viral infections for which there are currently few effective therapeutic remedies.

It is an object of the present invention to retard, preferably block, adhesion of pathogenic organisms and, thus, prevent or treat microbial or viral infection of the human or animal body.

It is a further object of the present invention to combine the retarding or blocking of adhesion with an inhibition of growth, thereby achieving an even greater utility.

It is a still further object of the present invention to achieve these utilities by the use of a benign material such as, but not limited to, milk serum since this facilitates much more frequent use than is considered prudent with many aggressive chemically based medicines.

Statements of Invention

In a first embodiment, this invention relates to the use of at least one milk apoprotein to prevent or treat microbial or viral infection of the human or animal body. Without wishing to be bound by this, it is believed that this is effected by inhibition of adhesion of potential pathogenic species. Specifically, the milk serum protein back-bone more correctly termed the milk serum apoprotein, which is left after the conjugated lipid and/or carbohydrate is removed from milk lipoproteins and milk glycoproteins, exhibits potent, broad-spectrum inhibition of adhesion of potential pathogens to human epithelial cells, as will be exemplified hereunder. When milk serum is used as a source, the residual apoprotein, stripped of its conjugated fatty acids and/or carbohydrate moieties, is amphoteric and inhibits the adhesion of bacteria or other pathogenic organisms to the host cell surface, thereby preventing first stage pathogenesis. An amphoteric protein has both a hydrophobic (fat-soluble) and hydrophilic (water-soluble) end. The cell surface of many microbial species has a lipid or glycolipid layer to which the hydrophobic end of the amphoteric protein is attracted. In this way, the apoproteins of milk serum coat the surface of the pathogenic organism, setting up a crude molecular barrier, which prevents the pathogenic organism (such as a fungus, bacterium or virion) achieving sufficient proximity to the host cell surface to establish adhesion.

Preferably, the aforementioned milk apoproteins are used with free fatty acids or their monoesters (including monoglycerides). As is known, free fatty acids and their monoglycerides are potent antimicrobial and antiviral agents against a wide variety of species, by inhibiting their growth. Thus, simultaneous or sequential (in either order) administration of at least one milk apoprotein and at least one free fatty acid or its monoester inhibits growth, as well as, inhibits adhesion of a wide range of microbial and viral species. A formation derived by hydrolyzing milk serum or milk whey contains both milk apoprotein(s) and free fatty acid(s).

Alternatively, the aforementioned milk apoproteins are used with short chain organic acids or their esters or salts. Thus, simultaneous or sequential (in either order) administration of at least one milk apoprotein and at least one short chain organic acid or its ester or salt inhibits growth, as well as, inhibits adhesion of a wide range of microbial and viral species.

Still more preferably, the aforementioned milk apoproteins may be used with both free fatty acids and their monoesters, as well as short chain organic acids and their salts and esters. Thus, simultaneous or sequential (in any order) administration of at least one milk apoprotein; at least one free fatty acid or its monoester; and at least one short chain organic acid or its ester or salt inhibits growth, as well as, inhibits adhesion of a wide range of microbial and viral species. A formulation containing all three components can be prepared by hydrolysing milk serum or milk whey.

In this invention, the use of at least one milk serum apoprotein or a mixture thereof, optionally with at least one free fatty acid or a monoester thereof or a mixture thereof, and/or optionally at least one short chain organic acid or its salt or ester, or a mixture thereof will be shown to be useful in the treatment of antibiotic resistant infections of the gastro-intestinal and oropharyngeal tract, the mucosal epithelium and the skin.

While infections from organisms such as MRSA and VREF, and many viral infections present an acute threat to health, there are seemingly less innocuous agents which are common commensals of the body and which may give rise to discomfort or disease in the longer term. One example of this is the generation of dental caries by the bacterium *Streptococcus mutans*. Dental caries is normally considered a cosmetic problem and is treated as such by the dental profession. There is, however, evidence to suggest that colonisation of the mouth by *Streptococcus mutans* may generate antibodies which, in systemic circulation, may cross-react with cardiac tissue giving rise to long-term heart disease and autoimmune damage to other organs.

In this invention the use of milk serum apoprotein(s) are shown to inhibit adhesion of *Streptococcus mutans* and so provide a useful adjunct in the prophylaxis of dental caries with consequential longer term health benefits.

The yeast *Candida albicans* is a common inhabitant of the skin and mucus membranes of many individuals where it is carried asymptomatically. *Candida* colonises the mucus membranes by first adhering to the surface of a mucosal epithelial cell from where it proliferates and infiltrates the cell lumen causing thrush.

Constituents of mucus secreted from these tissues normally inhibit adherence and proliferation; in some individuals, there is a debilitation of the normal secretory capability and a pathogenic process is established. The use of milk serum apoprotein(s) (adhesion inhibitory) and free fatty acid(s) or their monoesters and/or organic acid(s) or their salts or esters (both growth inhibitory) will provide suitable prophylaxis in those individuals subject to recurring thrush.

Viral infections do not respond to conventional antibiotics. While specialised anti-viral medicaments are available such as 'Acyclovir' for example used in the treatment of *Herpes simplex*, in general these are expensive and limited to a very narrow range of viral infections. While many viral infections have a systemic aspect, some have topical symptoms manifest as skin rash, blisters and sores, which frequently cause the greatest discomfort to the individual affected. The use of topical applications of formulations containing milk serum apoproteins with free fatty acid(s) and their monoesters will provide local anti-viral activity which, when used as an adjunct to systemic anti-viral treatment, will alleviate the external symptoms.

FAMVIR® is a proprietary formulation of Acyclovir (Smith Kline Beecham) designed as a systemic anti-viral agent for oral administration in the treatment of secondary infections of Varicella zoster (shingles). The Varicella virus causes chickenpox in primary infections with extensive skin eruptions of pus-filled vesicles, which rupture and form scabs. The infection causes intense itching and, when scratched, the sores may leave excessive scarring. The virus remains dormant for many years after recovery and may become reactivated by stress or immunocompromising conditions—the secondary infection is known as shingles and is characterized by an extremely painful skin rash. The use of topical formulations containing milk serum apoprotein(s) and free fatty ester(s) and monoesters thereof as described herein will minimize the superficial symptoms on the skin and act as a useful adjunct to the conventional anti-viral therapy. Equally other infections where there is a superficial (skin) dimension such as Rubella (measles) and Herpes (cold sores) are suitable clinical indications for topical applications.

The Standard Formulation as described hereinafter, which is hydrolysed milk serum or milk whey, is expected to be effective against pathogenic organisms at a concentration in the range of 0.5 to 25 mg/ml. It will, of course, be appreciated that the concentration required will depend on the number of pathogenic organisms, to be encountered and the relative concentrations thereof. Equally, the concentration ranges desired for the apoprotein(s); for the free fatty acid(s); and for the organic acid(s) will also depend on the number of pathogenic organisms to be encountered and their relative concentrations.

Free Fatty Acids

A free fatty acid is an organic acid, comprising a hydrocarbon chain with at least one carboxylic acid functional group, the latter being usually, although not necessarily, at a terminal position. Fatty acids can be either saturated, where all carbon to carbon bonds in the hydrocarbon chain are single, or unsaturated, where there is at least one carbon to carbon double or triple bond in the hydrocarbon chain. The free fatty acids or their monoesters are preferably naturally occurring or, alternatively, released by, for example, hydrolysis from naturally occurring sources such as, but not limited to, milk serum, egg yolk and vegetable oils.

Preferably, the useful antimicrobial and antiviral free fatty acids are saturated or unsaturated and have a hydrocarbon chain with an even number of carbon atoms (C 4-24), or a mixture thereof.

Suitable unsaturated free fatty acids have a hydrocarbon chain with C 14-24 and are preferably selected from palmitoleic (C16:1), oleic (C18:1), linoleic (C18:2), alpha and gamma linolenic (C18:3), arachidonic (C20:4), eicosapentanoic (C20:5) and tetracosenoic (C24:1) acids, in which the bracketed figures represent the number of carbon atoms in the hydrocarbon chain with the number of double (or triple) bonds following the colon representing the degree of unsaturation.

Suitable saturated fatty acids have a hydrocarbon chain with C4-C18 and are preferably selected from butyric or isobutyric (C4:0), succinic (C4:0), caproic (C6:0), adipic (C6:0), caprylic (C8:0), capric (C10:0), lauric (C12:0), myristic (C14:0), palmitic (C16:0) and stearic (C18:0) acids, which are effective against fungi and the gram-negative bacteria, coliforms and Staphylococci.

It should be appreciated that the free fatty acid(s) or their monoesters, whether naturally occurring or not, may be modified by chemical substitution including, but not limited to, short chain alkylation such as methylation or acetylation; esterification; and many other derivitisations to modify antimicrobial potency and such modified free fatty acids are also intended to form part of the present invention. However, for the purposes of the present invention, it is preferred to use naturally occurring, unmodified free fatty acid(s) or mixtures thereof or their monoesters, preferably their monoglycerides, such as those released from naturally occurring fat reservoirs selected from milk serum, egg yolk and vegetable oils.

Hydrolysis of the lipid content of milk serum provides a suitable mixture of free fatty acids from which broad-spectrum inhibition of microbial and viral growth may be usefully obtained for therapeutic or prophylactic purposes. The following table provides a typical breakdown of the fatty acid composition of milk serum lipid.

TABLE 1

Fatty Acid Composition of Milk Serum Lipid

| | | |
|---|---|---|
| Butyric | (C4:0) | 4% |
| Caproic | (C6:0) | 2.1% |
| Caprylic | (C8:0) | 1.2% |
| Capric | (C10:0) | 2.6% |
| Lauric | (C12:0) | 3.0% |
| Myristic | (C14:0) | 10.6% |
| Palmitic | (C16:0) | 27% |
| Palmitoleic | (C16:1) | 2.3% |
| Stearic | (C18:0) | 12.8% |
| Oleic | (C18:1) | 26% |
| Linoleic | (C18:2) | 2.3% |
| Linolenic | (C18:3) | 1.6% |
| Water | | Balance to 100% |

Organic Acids

Suitable organic acids, if present, have a short hydrocarbon chain (for example, C2-6) with at least one carboxylic acid functional group. The term "acid" is intended to embrace their salts or esters. The hydrocarbon chain may be saturated or unsaturated, straight or branched, substituted or unsubstituted. Suitable organic acids include glycolic, oxalic, lactic, glyceric, tartronic, malic, maleic, fumaric, tartaric, malonic, glutaric, propenoic, cis or trans butenoic, and citric acids. Of the organic acids, citric acid, which is a three-carbon chain with three carboxylic acid moieties, is preferred. Citric acid is produced during mammalian metabolism of carbohydrates and is a weak organic acid, which may be neutralised by an alkaline solution such as sodium hydroxide to give the sodium salt—sodium citrate. As such, it exists naturally in the body in low concentrations. As shown and claimed in this invention, when sodium citrate is added to milk serum apoproteins as described above, the potency of the fatty acids may be amplified with respect to in vitro cultures of particular bacteria.

Antimicrobial and Antiviral Utilities

Due to the polyspecific nature of inhibition of adhesion which may be achieved using milk serum apoprotein(s), alone or due to the polyspecific nature of inhibition of adhesion and inhibition of growth using milk serum apoprotein(s) in combination with free fatty acid(s) and/or organic acid(s), there is a very diverse range of potential pathogens that may be addressed.

Included among the gram-positive bacteria of significance are the Streptococci, *Lactobacilli, Corynebacteria, Propionibacteria*, Actinomycetes, *Clostridia, Bacillus* and *Enterococcus*.

Gram negatives include Staphylococci and the Enterobacteria, *Escherichia, Salmonella, Shigella,* and *Chlamydia* species are also sensitive.

Among the fungal species, the yeast *Candida albicans* has been shown to be sensitive, as well as the dermatophytes including *Trichophyton* species.

The protozoans of significant sensitivity include *Entamoeba histolytica, Giardia lamblia* and *Cryptosporidium neoformatans*.

The term "microbial" is intended to embrace bacteria, fungi and protozoans. Included among the enveloped virions of significance are *Herpes viridae, (Herpes simplex,* Varicella-zoster, and Epstein-ban); Poxviridae, (Orthopoxvirus and Avipoxvirus); Togaviridae, (Alphavirus, Flavivirus, Rubivirus and Pestivirus); Coronaviridae, (bronchitis virus); Retroviridae (Human T-cell leukaemia and Human Immunodeficiency virus); Influenza virus, Lyssavirus, California Encaphalitis Virus, Lassa Virus, Paramyxovirus, Pneumovirus and Morbillivirus.

Pharmaceutically and Cosmetically Acceptable Delivery Systems

A pharmaceutically acceptable delivery system comprising a pharmaceutically or cosmetically effective amount of at least one milk serum apoprotein, with or without a pharmaceutically or cosmetically effective amount of at least one free fatty acid and their monoesters and/or a pharmaceutically or cosmetically effective amount of at least one organic acid and their esters or salts may be administered to achieve a clinically useful effect.

Ointments provide a useful delivery mechanism to relieve the superficial symptoms of viral and bacterial infections manifest in skin rash, blisters and pustules, included among which are herpes, shingles, acne and infectious dermatitis.

Bandages and wound dressings may be impregnated to achieve sustained release of the active material at the site of an infection.

Particularly in the case of methicillin resistant *Staphylococcus aureus*, the delivery system may comprise a nasal spray for de-contamination of known carriers. The use of a delivery system in the form of a skin lotion will provide topical decontamination of skin and hair.

The delivery system may comprise eye drops for the treatment or prevention of infection, of the eye.

The delivery system may comprise intravaginal creams or gels, for example, hydrating and lubricating gels, or pessaries commonly used in feminine care to prevent recurring infections of the yeast *Candida albicans* and as a protection against exogenous bacterial and viral disease.

The delivery system may comprise a post-surgical wound dressing in which the active agent(s) is/are distributed in a sustained release polymer. Such a delivery system may be used to minimise nosocomial infections arising from MRSA and other antibiotic resistant bacteria.

The delivery system may additionally comprise antioxidant excipient(s), and be administered parenterally or by IV infusion to achieve a systemic anti-viral and/or anti-microbial effect.

The delivery system may alternatively or additionally comprise a milk-like drink or a food, in which the active agent(s) may be enteric coated to facilitate its transport through the stomach to the intestine, where the active agent(s) can be used as a prophylactic agent against intestinal infections, including Pseudomembraneous colitis.

The delivery system may comprise oral hygiene products such as chewing gums, mouthwash, toothpaste and denture adhesives and fixatives to achieve reduced caries, and dental plaque and to provide long-term protection against gingivitis, periodontitis and recurring thrush.

The delivery system may comprise processed foods, in which the active agent(s) prevent microbial and/or viral spoilage and the potential for food-borne illness arising from organisms such as *Salmonella* and *Campylobacter*.

DESCRIPTION OF THE DRAWINGS

Diagram 1 illustrates four separate size Exclusion chromatograms and these are marked A, B, C and D.

A). Time 0 hours, pre-treatment: A front running peak at Rt 7.174 minutes illuminated at 280 nm has an underlying peak visible at 330 nm. The 330 nm absorbance comes from the lipid moiety conjugated to the large proteins that constitute this primary fraction.

B). Time 2 hours after treatment commenced: the primary peak at 7.174 minutes has been degraded with contemporaneous increase in two late running fractions at Rt 9.7 and 10.6 minutes. The 330 nm lipid fraction has been degraded and there is no visible increase in the 330 nm absorbance with the late running peaks.

C). Time 8 hours: shows further degradation of the lipid fraction with no significant change to the late running 280 nm proteins.

D). Time 16 hr: extended incubation shows no change in the overall profile at either wavelength.

Diagram 2 uses the adhesion of *Candida albicans* to Buccal Epithelial Cell as a measurement of efficacy of the test material, milk serum, before and after enzyme hydrolysis is illustrated. The 'Control' represents the average total adhesion (36%) achieved with no inhibitory substances present Milk serum before hydrolysis at 1 mg/ml and 2 mg/ml gave some 39% inhibition of the control adhesion (22% adhesion, down from 36% adhesion). At 5 mg/ml pre-hydrolysis, 45% inhibition of adhesion is achieved. The same material is shown at the same concentrations after enzymatic hydrolysis. 1 mg/ml is apparently less effective than the same material pre-hydrolysis, however at 2 mg/ml there is 62% inhibition (compared to 39%), and at 5 mg/ml there is 100% inhibition of adhesion, compared to 45% pre-hydrolysis.

Diagram 3 shows the relative inhibition of *Candida* adhesion achieved from each of the lipid and protein fraction of the Standard Formulation. The 'control' is at 45% adhesion. The protein fraction at 1 mg/ml is showing 19% adhesion (58% inhibition), at 2 mg/ml adhesion is down to 3%, being 94% inhibition, and totally blocked at 5 mg/ml. In comparison, there is no visible adhesion inhibitory effect from the lipid fraction at any concentration.

Diagram 4 showing, using the same lipid and protein fraction illustrated in Diagram 3, the relative growth inhibitory properties of the lipid fraction on the growth of *Candida albicans* at 10, 8, and 6 mg/ml. There is a progressive increase in growth inhibitory properties as concentration increases with visible destruction of the yeast culture at 10 mg/ml based on loss of Optical Density.

Diagram 5 shows the effect of the protein fraction from Diagram 3 above using the growth of *Candida albicans*. There is no apparent inhibition of growth arising from the protein fraction at any of the concentrations tested.

Diagram 6 shows the *Candida* growth inhibitory properties of the Standard Formulation at 0, 1 and 5 mg/ml, 90% inhibition is achieved at the highest concentration.

Diagram 7 shows an intervention growth assay where the inhibitory substances are added after 5 hours of normal growth of *Candida albicans*. The immediacy of the inhibition at concentrations of 8 and 6 mg/ml is apparent. At lower concentrations the effect is slower but overall inhibition is as effective at 4 mg/ml and some inhibition is also evident at 2 mg/ml.

Diagram 8 shows the *Candida* adhesion inhibitory properties of the Standard Formulation at 1, 2 and 5 mg/ml where the yeast has been pre-treated by exposure to the test substance for 10 minutes prior to being exposed to Buccal Epithelial Cell. At 1 mg/ml there is 53% inhibition of adhesion, while no adhesion occurs at 2 and 5 mg/ml. The protein blank in this example is Bovine Serum Albumin at 1 mg/ml showing just 13% inhibition (relative to the Standard Formulation at 53%).

Diagram 9 shows the same Standard Formulation used in Diagram 8 above to pre-treat the Buccal Epithelial Cells for 10 minutes prior to being exposed to the *Candida* culture. At 1 mg/ml there is 55% inhibition of adhesion while adhesion is totally inhibited at 2 and 5 mg/ml. The protein blank in this example is De-ovalbuminised egg white at 1 mg/ml giving some 12% inhibition of adhesion.

Diagram 10 shows the Standard Formulation inhibiting growth of methicillin resistant *Staphylococcus aureus* (MRSA) by approximately 50% relative to the control where Phosphate Buffered Saline (PBS) is used as a test 'blank'. When the Standard Formulation is supplemented with 2, 4 and 5 mg/ml of sodium citrate, growth is progressively inhibited to zero at the higher concentrations.

Diagram 11 shows the inhibitory properties of the Standard Formulation against adhesion of MRSA to Buccal Epithelial Cell compared with sodium citrate and BSA.

At 5 mg/ml the Standard Formulation achieves 98% inhibition of adhesion, while at the same concentration sodium citrate is inhibiting at approximately 10%, there is no effect from the protein blank.

Diagram 12 shows that the growth of the dental caries causing organism *Streptococcus mutans* is inhibited by 5 mg/ml of the Standard Formulation, under the test conditions described in the text.

Diagram 13 shows that *Streptococcus mutans* adheres to hydroxyapatite beads, used here as a surrogate for dental enamel. The standard Formulation at 0.8 mg/ml achieves approximately 100% inhibition of adhesion under the test conditions. Sodium citrate affects adhesion of this organism by some 10% at 0.8 mg/ml while Bovine Serum Albumin used as a protein blank achieves some 30% inhibition under these test conditions.

Methods and Materials:

Milk serum proteins may be extracted from whole fresh milk, preferably from whole fresh ruminant milk, by first separating the butter-fat using centrifugation. The supernatant is then acidified to pH 4.5, at which point the caseins precipitate. Further centrifugation will leave a clear supernatant containing the milk sugar lactose, the milk serum proteins and dissolved minerals. Lactose, which represents a substantial proportion of the solids content of milk serum (up to 50%), is then removed by dialysis or ultra-filtration. The resultant "conjugated protein-rich" fraction will have a composition approximating to the following (v/v):

| | |
|---|---|
| Beta-Lactoglobulin | 56% |
| Alpha-lactalbumin | 11% |
| Gamma-globulin | 12% |
| Serum albumin | 6% |
| Lactoferrin | 4% |
| Mucins | 2% |
| Enzymes | 1% |
| Minor proteins | 1% |
| Protein bound lipid (fat) | 7% |

Many of these proteins are complex lipoproteins or glycoproteins with substantial non-protein macromolecules conjugated to them, but the major protein component of whey from ruminant mammals is beta-lactoglobulin, which may represent up to 70% of whey and 90% of colostrum (the first milk after parturition). Beta-lactoglobulin is a lipoprotein, with substantial amounts of the isoprenoid, retinol, conjugated to it, but lipids and fatty acids make up a substantial portion of the non-protein component.

Alternatively, a convenient source of milk serum proteins is dairy industry whey powder, which may be obtained commercially from many different sources. In many cases, commercial suppliers have already removed the lactose content, providing a "conjugated protein-rich" material with a fat content of between 6 and 10%, such material being the preferred source material for use in this invention. Whilst some commercial suppliers use Ultra High Temperature (UHT) to increase shelf life of liquid whey, such treatment denatures the protein back-bone and renders the material useless for the purposes described herein. Where the fat content is below 6%, it may be supplemented by adding butterfat back to the whey powder, when it is re-constituted (in purified water (water purified by reverse osmosis)) for enzyme hydrolysis as described herein.

A suitable commercial source of standardised low lactose whey powder is 'Carbelac 80' a whey protein concentrate from Carbery Milk Products, Ballineen, County Cork, Ireland.

Inhibition of Growth Assay

The inhibition of growth of various bacteria or yeast may be demonstrated by growing the organism in a suitable medium with and without test substances such as milk serum apoproteins, free fatty acids/monoesters and/or organic acids/salts/esters; the test format being suitably constructed with media blanks and controls. A microtitre plate assay may be used to increase the number of test points and growth is measured using optical density determination.

In order to ensure that there is no dilution effect arising from the addition of different concentrations of test material, test solutions are prepared by dissolving or suspending the appropriate amount of test substance, in the appropriate fresh growth medium for that bacteria or yeast. Typically, test solutions are prepared from a stock solution with a concentration of 20 mg/ml, prepared by dissolving, for example, 200 mg of test substance in a final volume of 10 ml of fresh growth medium. The stock solution is centrifuged at 6,000 rpm for 10 minutes to remove suspended solids. The stock solution is then aseptically diluted using appropriate volumes of the stock solution and fresh growth medium, to achieve test concentrations of, for example, 10, 8, 6, 4, 2 mg/ml.

The dilution step to achieve say 10 mg/ml from a 20 mg/ml stock solution is described herein as 1:2 and by this is meant one volume of stock solution is diluted with 1 volume of diluent, to achieve a final volume of 2 volumes. This convention will be used herein to refer to all dilution steps used herein.

Prepared solutions are pre-warmed to 37° C. 100 microliters is added to each well as required immediately before addition of 100 microliters of the prepared inoculum. Thus, a test concentration of 10 mg/ml is subjected to a further 1:2 dilution in the test well, so that the "10 mg/ml" is actually 5 mg/ml in the test well itself. The Multiskan Ascent has an automatic shake cycle that is used to ensure even distribution of culture prior to each OD reading.

Concerning inhibition of growth of Candida albicans, a 'Nunc' 96 well microtitre plate (Nalge Nunc International, Copenhagen, Denmark) is used, each well of which holds the aforementioned 200 microliters. Test points are conducted in quadruplicate. The inoculum consists of 100 microliters of freshly grown bacteria, or yeast prepared as described below. The final volume in each well consists of a total of 200 microliters, comprising 100 microliters of the appropriate dilution of test substance and 100 microliters of inoculum in fresh medium.

Inoculated plates are loaded into a 'Multiskan Ascent' (LabSystems, Helsinki, Finland) incubated microtitre plate reader and held at 37° C. for a period of up to 18 hours during which optical density changes in the wells are measured at 600 nm every hour. At the end of the growth cycle, the results are processed by averaging each of the quadruplicate wells, and illustrating the changes graphically.

Yeast:

12 hour (overnight) culture of Candida albicans in Oxoid Yeast Minimal Media with 5% (w/v) glucose added (Oxoid is a trademark), diluted 1:10 (one to a final volume of 10) (v/v) with fresh medium at 37° C., add 100 microliters to each well.

The yeast Candida albicans has an optimal pH for growth of between 4.0 and 4.5 and many of its pathogenic processes are also optimal in this pH range. The growth assay described above may be modified with the use of 50 mM sodium lactate buffer at pH 4.0 to prepare the yeast minimal media and the test solution, so as to more adequately reflect the in vitro environment wherein the Standard Formulation will be effective.

A similar methodology may be used to measure growth, and inhibition of growth, of bacteria (and fungi) by modifying the growth media accordingly. In case of Streptococcus mutans and Staphylococcus aureus, both shown herein as examples, the growth media is Oxoid Brain Heart Infusion Broth (Oxoid is a trademark).

Adhesion Assay:

Measurement of adhesion, and inhibition of the same, requires selection of a suitable substrate and a method of enumerating number of organisms adhering (or not) to that substrate. Most potential pathogenic organisms adhere to mucosal epithelial cells and a convenient source of a representative mucosal epithelial cell may be easily harvested from inside the cheek. Buccal epithelial cells (BEC's) are harvested by scraping the mucosal membranes in the mouth using a wooden tongue depressor as follows.

Harvesting of Buccal Epithelial Cells:

Standard wooden tongue depressors as used in clinical examination of the mouth are wrapped, in tin foil and autoclaved. 5.0 ml aliquots of 0.1M potassium phosphate containing 0.9% (w/v) sodium chloride pH adjusted to 6.8 (i.e. PBS) are placed in sterile 25 ml sample bottles. Tongue depressors are then used to rub the inside of a volunteer's cheek and the collected scrapings are transferred to the PBS containers. The collected samples are centrifuged at 1,000 rpm for 3 minutes to sediment the BEC's, leaving bacteria and other oral detritus in suspension. The supernatant from these tubes is decanted and a further 5 ml of fresh sterile PBS added, the BEC's are re-suspended and re-centrifuged twice to achieve 'washed cells'.

There are many different methods of enumerating bacteria and yeast, all of which are well known to those skilled in the art and these include viable plate counting, direct microscopic counting, radio-scintillation labelling and fluorescent labelling. Any validated method of enumeration is suitable, provided it does not interfere with the organism's ability to adhere to the chosen substrate.

In the examples given hereunder, direct microscopic counting has been chosen for the yeast Candida and a fluorescent label for bacteria. More importantly, however, the number of yeast and bacteria not adhering from a standard population have been enumerated, as distinct from endeavouring to count adhering cells, because the substrate usually interferes with the count.

The basis of the technique involves exposing a standardised (known) number of yeast or bacteria to a standardised substrate (number of BEC's), allowing a 60 minute incubation period for the cells to adhere and then filtering the combined population through a 10 micron nylon mesh. The mesh will retain BEC's and those yeast or bacteria adhering to them, non-adhering yeast or bacteria will be washed through, where they may be enumerated in the filtrate and expressed as a percentage of the original population not adhering; percent adherence being the inverse of this.

Direct microscopic counting of yeast and BEC is conducted using a graduated haemocytometer slide and the method is well known to those skilled in the art.

Fluorescent labelling of bacteria is conducted after adhesion (on those cells in the filtrate) using fluorescent dyes such as BCECF/AM (Calbiochem Biosciences Inc., La Jolla, Calif.) and Syto 13 (Molecular Probes, Oregon, USA). Labelling methods are as described by the manufacturers of the dyes. The amount of fluorescence is measured in a fluorimeter (Fluroscan from Lab-Systems, Helsinki, Finland) and is in direct relationship to the number of bacteria present.

The following general method may be used to measure adherence of the yeast Candida albicans to BEC and the inhibition of that adherence using the formulation of milk serum apoprotein(s) as described above. The same general method is suitable for measuring inhibition of adherence of Staphylococcus aureus to BEC's and also inhibition of adherence of Streptococcus mutans, with the exception that the substrate for Streptococcus mutans, is powdered hydroxylapatite available from Merck and used as a surrogate for dental enamel.

A fresh clinical isolate of Candida albicans is preferred as many of the type cultures have lost virulence in culture collections. If a clinical isolate is not available, C. albicans type strain ATCC 10231 may be used to achieve representative results (ATCC is the American Type Culture Collection housed in Maryland USA).

The yeast is routinely cultured on Oxoid Malt Extract Agar (Oxoid is a trademark). Oxoid Yeast Extract Peptone Dextrose broth is used for liquid cultures, these are inoculated from fresh agar plates and incubated with agitation at 37° C. for 10 hours. After ten hours, the yeast is harvested by centrifugation and washed in sterile PBS at pH 6.8.

Both the washed BEC's and the freshly grown washed yeast cells are counted microscopically and the concentrations adjusted such that the yeast is in the order of $1 \times 10^5$ and BEC's at $1 \times 10^3$. Equal volumes of the two solutions when mixed will give a ratio of 100 yeast cells per BEC.

In testing various concentrations of test substances such as milk serum apoprotein(s), these are added in the desired strength to the PBS (pH 6.8) used in the final suspension of either yeast or buccal cells. Typically, concentrations of 5, 2 and 1 mg per ml are used and tests are conducted to determine the effectiveness of the formulation at inhibiting adhesion by pre-coating BEC's or pre-coating the yeast. A period of just ten minutes is allowed as 'pre-coating' prior to combining with the other of the two suspensions when adhesion begins. The formulation is shown to be effective in either pre-coating of Buccal Epithelial Cells or pre-coating of Candida albicans. Thus, greater utility may be achieved by creating a protective molecular barrier on either or both of these surfaces. Specifically, pre-coating Buccal Epithelial Cells will prevent adhesion being established whilst pre-coating the pathogenic organism, in this case yeast, will prevent an already established colony from extending to other areas.

Equal volumes of the two solutions/suspensions are mixed and incubated with gentle agitation for 60 minutes, after which the mixture is filtered through a nylon mesh with a defined porosity of 10 microns. The number of yeast in the filtrate are counted microscopically and expressed as a percentage of the original population. When high virulence clinical isolates are used, it is not unusual to achieve up to 40% adherence.

EXAMPLE 1

Preparation of Milk Serum Free Fatty Acids and Milk Serum Apoproteins

Lactose free whey powder (Carbelac 80 from Carbery Milk Products) is the starting material. Carbelac 80 is typically 100% whey, of which typically 0% is skim, 80% is protein, 5% is moisture, 8% is fat and 3% is ash. 30 grams of this starting material is dissolved to a final volume of 1 liter of phosphate buffered saline (PBS) at pH 6.8. To this is added 1 gram of a suitable composition of various esterase (mainly lipases, but also amylases and proteases) enzymes, for example, 'Lipase Type 2 Crude from porcine pancreas' available from Sigma. The mixture is incubated at 37° C. for 18 hours; heat-treated at 60° C. for 10 minutes to inactivate the enzyme; and spray dried. Other suitable esterase enzymes include, but are not limited to, 'Palatase' and 'Novozyme' commercially available from Novo Nordisk, Copenhagen, Denmark and used in a 50:50 mix (w/w) at 1 gram per 30 gram of lactose free whey.

The course of the apoprotein and free fatty acid/monoglyceride formation may be followed chromatographically as illustrated in Diagram 1. Gel filtration (size exclusion) HPLC using Sephacryl S-200 and PBS (pH 6.8) as an elution buffer will give adequate resolution to illustrate the main events during enzymatic hydrolysis. Use of two wavelengths to monitor the eluent is advantageous; at 280 nm the proteins are illuminated while use of a 330 nm wavelength illuminates the lipid/carbohydrate component conjugated to these proteins. A front running peak at Rt (retention time) 7.174 minutes (Diagram 1A) represents the early elution of large proteins and the lipid component is visible as an underlying peak. During the course of hydrolysis (Diagrams 1B (2 hours) and 1C (8 hours)), the front peak and its conjugated lipid/carbohydrate disappear, with a commensurate increase in the concentration of two late running fractions (280 nm) at 9.7 and 10.6 minutes, these being smaller proteins and the apoproteins from the front peak. Diagram 1D shows that extended hydrolysis (16 hours) shows no further change in Rt at either wavelength.

Using procedures as outlined above, a typical composition of enzyme treated lactose free whey (or apoprotein-rich and free fatty acid-rich fraction) will consist of the following "Typical Formulation".

| COMPONENT | % (v/v) |
|---|---|
| Apoprotein of Beta-lactoglobulin | 25-35 |
| Apoprotein of Fat Globules | 5-15 |
| Free fatty acids | 15-25 (see Table 1) |
| Residual Lipid (includes cholesterol) | 5-15 |
| Apoprotein of Alpha-lactoglobulin | 5-15 |
| Apoprotein of Gammaglobulin | 6-10 |
| Serum albumin | 1-3 |
| Alpha-tocopherol | 2-6 |
| Sodium citrate | 2-6 |
| Sodium phosphate | 1-3 |

The apoprotein preparation procedure may be enhanced by the addition of surfactants such as purified components of bile salts such as cholic acid and/or by the addition of suitable enzyme co-factors such as calcium salts and/or by the addition of suitable buffers such as sodium citrate. In some applications such as the inhibition of growth of MRSA, the residual sodium citrate also contributes to growth inhibitory properties but not inhibition of adhesion. The stability of the free fatty acids and their monoglycerides may be enhanced by the addition of anti-oxidants such as, for example, alpha tocopherol (vitamin E).

The gamma-globulin (immunoglobulin) content of whey may be manipulated by immunisation of the donor animal Immunisation procedures are well known and the specificity of the immunoglobulins may be tailored and amplified towards any particular organism using attenuated strains of that organism in the vaccine. Whilst the use of such immune wheys fall within the scope of the present invention, the use of non-immune whey, where the 'native' gamma-globulin has no particular specificity for any organism, is preferred.

This resulting hydrolysed material exhibits inhibition of growth and inhibition of adhesion as illustrated in the following Examples using the Streptococcus mutans, the dental caries organism, the yeast Candida albicans and methicillin resistant Staphylococcus aureus.

The "Standard Formulation" as described and exemplified hereinafter comprises (v/v):

| | |
|---|---|
| Apoprotein of Beta-lactoglobulin | 32% |
| Apoprotein of Fat Globule Membrane | 8% |
| Free fatty acids | 22% (see Table 1) |
| Residual Lipid (includes cholesterol) | 8% |

-continued

| | |
|---|---|
| Apoprotein of Alpha-lactoglobulin | 10% |
| Apoprotein of Gammaglobulin | 8% |
| Serum albumin | 2% |
| Alpha-tocopherol | 5% |
| Sodium citrate | 3% |
| Sodium phosphate | 2% |

The hydrolysis procedure activates adhesion inhibitory properties that are not present in pre-activated whey. Diagram 2 illustrates this effect, by comparing pre-hydrolysis and post hydrolysis milk serum (the latter being the Standard Formulation) on the inhibition adhesion of *Candida albicans* to Buccal Epithelial Cells. As will be observed, whilst unhydrolysed milk serum shows some inhibition of adhesion, there is a marked, concentration-dependent inhibition of adhesion in the presence of hydrolysed milk serum, so that no adherence of *Candida albicans* is detected at 5 mg/ml.

Separation of Milk Serum Apoproteins:

The Standard Formulation may be fractionated using a chloroform:methanol extraction procedure to separate the lipid and apoprotein fractions.

The procedure was performed using a concentration of the Standard Formulation at 10 mg/ml of phosphate buffered saline at pH 6.8. One ml of this solution was added to glass tubes containing 5 ml of chloroform and 2.5 ml of methanol. The mixture was vortexed for 30 seconds and then agitated for 30 minutes, after which it was allowed to stand until separation of the solvent layers was complete. Using a Pasteur pipette, the upper methanol layer was removed. Aliquots of each solvent fraction were vacuum dried. Any polar compounds (proteins) are present in the polar solvent (methanol) fraction, and non-polar (fatty acids) will be retained in the chloroform layer. The dried methanol fractions were taken up in one tenth their original volume in phosphate buffered saline at pH 6.8 and the dried chloroform fraction was taken up in one tenth the original volume of ethanol, and diluted in PBS for test purposes.

Diagram 3 illustrates the adhesion inhibitory properties of both the apoprotein-rich and lipid-rich fractions, concentration-dependent inhibition of adhesion being associated with the apoprotein-rich fraction and not the lipid fraction. Indeed, at 5 mg/ml, virtually no adhesion of *Candida albicans* could be detected. Diagram 4 illustrates the concentration-dependent growth inhibitory properties of the lipid-rich fraction on *Candida albicans*, while Diagram 5 shows that the apoprotein rich fraction has no effect on growth (there is in fact some amplification of growth at 10 mg/ml from the increasing concentration of protein fraction).

EXAMPLE 2

Using the growth assay described in Methods and Materials above, the growth inhibitory properties of the Standard Formulation against a fresh clinical isolate of *Candida albicans* was evaluated. The assay was a microtitre plate format and each test concentration was conducted in quadruplicate. Growth was measured at 600 nm over a 20-hour period and the results are illustrated in Diagram 6. The Standard Formulation (at 5 mg/ml) gave almost 90% inhibition of growth, relative to the control with 0 mg/ml of the Standard Formulation added. The Standard Formulation at 1 mg/ml gave an intermediate result.

Using a similar assay procedure, with the exception of adding the test substances after 5 hours of normal growth, is described herein as an intervention assay. The Standard Formulation is added at concentrations ranging from 0 mg/ml to 8 mg/ml. The test concentrations are set-up such that there is similar dilution effect in all wells when pre-warmed (to 37° C.) test solutions are added. The results of an intervention assay on a fresh clinical isolate of *Candida albicans* are presented in Diagram 7, the data having been processed to remove the optical density change at 5 hours resulting from the addition of test material. The immediate and dramatic, concentration dependent, inhibitory effect of the Standard Formulation on the growth of *C. albicans* is evident at concentrations of 8, 6, 4 and 2 mg/ml.

EXAMPLE 3

The Standard Formulation inhibits adhesion as well as growth. The adhesion assay method has been described in Methods and Materials above. Using the same formulation as in Example 2, the inhibitory effects on the adhesion of the same fresh clinical isolate to BEC's are illustrated in Diagrams 8 and 9.

In Diagram 8, the yeast cells have been exposed to the Standard Formulation for 10 minutes prior to being added to the BEC's. In Diagram 9, BEC's have been exposed to the Standard Formulation for 10 minutes prior to being added to the yeast suspension.

The 'Control' in both of these assays represents the adhesion achieved under the test conditions when no inhibitory substances are present; 41% and 35%, respectively. The addition of the Standard Formulation at 1 mg/ml in *Candida* pre-treatment reduces adhesion to 20% (53% inhibition), while the same concentration in BEC pre-treatment reduces adhesion to 16% (55% inhibition). At 2 and 5 mg/ml of the Standard Formulation in both pre-treatment of yeast and BEC's, there is 100% inhibition of adhesion under the test conditions.

The "protein blank" in Diagram 8 is Bovine Serum Albumin and in Diagram 9, de-ovalbuminised egg white was used, both at 1 mg/ml, and both intended to indicate that the effect of the Standard Formulation is not 'simply' an effect due to protein concentration.

EXAMPLE 4

The effectiveness of the Standard Formulation against both growth and adhesion of methicillin resistant *Staphylococcus aureus* (MRSA) is demonstrated in Diagrams 10 and 11.

MRSA is routinely sub-cultured on blood agar and a single colony is used to inoculate a tube of Oxoid Brain Heart Infusion Broth as described in Methods and Materials above. After 8 hours, the innoculum is used in growth and adhesion assays using the methodologies described above.

MRSA is not as sensitive to free fatty acids/monoglycerides as other organisms and the addition of citrate salts, as are contained in the Standard Formulation, are essential for meaningful inhibition of growth of this particular organism. Diagram 10 illustrates the effect of the Standard Formulation at 5 mg/ml and with increasing concentrations of trisodium citrate (0, 2, 4 and 5 mg/ml), complete inhibition of growth is achieved when trisodium citrate at 4 or 5 mg/ml is added to the Standard Formulation of 5 mg/ml. Trisodium citrate is added to the test solutions while they are being prepared in the growth medium as described under "growth assay" methods. Specifically, as described, the stock solution of the Standard Formulation (concentration of 20 mg/ml) is mixed with an equal volume of a trisodium citrate solution (concentration 20 mg/ml). Thus, a 1:2 dilution is achieved in a solution containing 10 mg/ml of the Standard Formulation and 10 mg/ml trisodium citrate. As explained above, this composite formulation is, in the test well, a 5 mg/ml of the Standard Formulation and a 5 mg/ml trisodium citrate. Equally, of course, the stock Standard Formulation solution of 20 mg/ml may be mixed with an equal volume of a trisodium citrate solution containing 16 mg/ml or 8 mg/ml, so as to achieve a Standard Formulation supplemented with 4 and 2, respectively, mg/ml trisodium citrate as is shown in Diagram 10.

MRSA adheres to BEC's, and these are used here in a manner similar to that described for *Candida albicans*. Sodium citrate, alone, has no effect on adhesion of MRSA to BEC whilst, as illustrated in Diagram 11, almost complete inhibition of adhesion is achieved at 5 mg/ml of the Standard Formulation (no added sodium citrate) under the test conditions. Bovine Serum Albumin is used as a 'protein blank' and this material has no effect on the adhesion of MRSA to BEC's.

EXAMPLE 5

The organism *Streptococcus mutans* is considered to be the causative agent of dental caries, since it adheres avidly to the enamel surface of teeth. Fermentation of carbohydrate results in the secretion of lactic acid, bringing localised pH down to where there is dissolution of the dental enamel and the onset of dental caries.

Diagram 12 illustrates the effect of 5 mg/ml of the Standard Formulation on the growth of *Streptococcus mutans*. The test is conducted in the manner described for all growth assays above. At 5 mg/ml of the Standard Formulation, there is complete inhibition of growth of the organism over the 15 hours assayed. During the same period, the control growth, with Phosphate Buffered Saline at pH 6.8 added instead of the Standard Formulation, shows the expected logarithmic increase.

In measuring inhibition of adherence of *Streptococcus mutans*, hydroxyapatite powder from Merck was used as a surrogate for dental enamel. The test procedure is as described in Methods and Materials above, with the following modifications: 1 ml of fresh culture, adjusted to an optical density of 0.1 at 600 nm, is added to 5 mg of saliva coated hydroxyapatite beads; allowed to adhere for 1 hour; and centrifuged at slow speed to sediment the hydroxyapatite with adhering bacteria. The number of bacteria remaining in the supernatant are that percentage of the original population not adhering and are expressed as a percentage of the original population; the inverse being the percent inhibition of adherence.

Diagram 13 illustrates the dose-dependent, adhesion inhibitory effect of the Standard Formulation; almost complete inhibition being achieved at 0.8 mg/ml. Again in this example, Bovine Serum Albumin was used as a 'protein blank' and, in this test system, BSA is having an inhibitory effect of some 30% at 0.8 mg/ml, whereas sodium citrate shows some 10% inhibition of adhesion.

The invention claimed is:

1. A product comprising: (a) at least one milk serum apoprotein selected from the group consisting of (i) apolipoproteins, (ii) apoglycoprotcins, and (iii) a mixture of (i) and (ii), whereby said milk serum apolipoprotein is the protein moiety remaining after conjugated lipid is removed from milk serum lipoproteins, and said milk serum apoglycoprotein is the protein moiety remaining after conjugated carbohydrate is removed from milk serum glycoproteins; and (b) at least one free fatty acid.

2. The product according to claim 1, in which said free fatty acid is selected from the group consisting of palmitoleic, oleic, linoleic, alpha and gamma linolenic, arachidonic, eicosapentanoic, and tetracosenoic acids.

3. The product according to claim 1, in which said milk serum apoprotein is an apolipoprotein.

4. The product according to claim 3, in which said apolipoprotein is derived from a milk serum lipoprotein selected from the group consisting of beta-lactoglobulin, fat globule membrane, and a mixture thereof.

5. The product according to claim 1, in which the milk serum apoprotein is an apoglycoprotein.

6. The product according to claim 5, in which said apoglycoprotein is derived from a milk serum glycoprotein comprising gammaglobulin.

7. The product according to claim 1, in which said free fatty acid is either saturated or unsaturated and has a hydrocarbon chain with an even number of carbon atoms numbering between 4 and 24 carbon atoms.

8. The product according to claim 7, in which said free fatty acid is an unsaturated fatty acid having a hydrocarbon chain with a number of carbon atoms numbering between 14 and 24 carbon atoms.

9. The product according to claim 7, in which said free fatty acid is a saturated fatty acid having a carbon chain with a number of carbon atoms numbering between 4 and 18 carbon atoms.

10. The product according to claim 1, in which said free fatty acid is selected from the group consisting of butyric, isobutyric, succinic, caproic, adipic, caprylic, capric, lauric, myristic, palmitic, and stearic acids.

11. The product according to claim 1, further comprising at least one additional component selected from the group consisting of an organic acid, an organic acid salt, and an organic acid ester.

12. The product according to claim 11, in which said organic acid, organic acid salt, or organic acid ester is selected from the group consisting of glycolic, oxalic, lactic, glyceric, tartronic, malic, maleic, fumaric, tartaric, malonic, glutaric, propenoic, cis-butenoic, trans-butenoic, and citric acids, and their corresponding salts and esters.

13. The product according to claim 11, in which said organic acid, organic acid salt, or organic acid ester is selected from citric acid, and its corresponding salts and esters.

\* \* \* \* \*